US00PP20926P2

(12) United States Plant Patent
Spivey et al.

(10) Patent No.: US PP20,926 P2
(45) Date of Patent: Apr. 13, 2010

(54) CREPE MYRTLE PLANT NAMED 'BRADBERRY'S WINE'

(50) Latin Name: *Lagerstroemia indica*
Varietal Denomination: Bradberry's Wine

(75) Inventors: James Spivey, Devine, TX (US); Albert F. Stauder, III, San Antonio, TX (US)

(73) Assignee: Color Spot Nurseries, Fallbrook, CA (US)

( * ) Notice: Subject to any disclaimer, the term of this patent is extended or adjusted under 35 U.S.C. 154(b) by 0 days.

(21) Appl. No.: 12/313,683

(22) Filed: Nov. 21, 2008

(51) Int. Cl.
*A01H 5/00* (2006.01)

(52) U.S. Cl. ..... Plt./252

(58) Field of Classification Search ..... Plt./252
See application file for complete search history.

*Primary Examiner*—June Hwu
(74) *Attorney, Agent, or Firm*—C. A. Whealy

(57) ABSTRACT

A new and distinct cultivar of Crepe Myrtle plant named 'Bradberry's Wine', characterized by its upright to somewhat outwardly spreading plant habit; freely branching habit; dark green-colored leaves; large inflorescences with showy red purple-colored flowers; resistance to Powdery Mildew; and good garden performance.

2 Drawing Sheets

Botanical designation: *Lagerstroemia indica.*
Cultivar denomination: 'Bradberry's Wine'.

BACKGROUND OF THE INVENTION

The present invention relates to a new and distinct cultivar of Crepe Myrtle plant, botanically known as *Lagerstroemia indica* and hereinafter referred to by the name 'Bradberry's Wine'.

The new Crepe Myrtle plant originated from an open-pollination in 1993 of *Lagerstroemia indica* 'Zuni', not patented, as the female, or seed, parent with an unknown selection of *Lagerstroemia indica*, as the male, or pollen, parent. The new Crepe Myrtle plant was discovered and selected by the Inventors in 1996 as a single flowering plant from within the progeny of the stated open-pollination in a controlled outdoor nursery environment in San Antonio, Tex.

Asexual reproduction of the new Crepe Myrtle plant by softwood cuttings in a controlled greenhouse environment in San Antonio, Tex. since July, 1996 has shown that the unique features of this new Crepe Myrtle plant are stable and reproduced true to type in successive generations of asexual reproduction.

SUMMARY OF THE INVENTION

Plants of the new Crepe Myrtle have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Bradberry's Wine'. These characteristics in combination distinguish 'Bradberry's Wine' as a new and distinct cultivar of Crepe Myrtle:

1. Upright to somewhat outwardly spreading plant habit.
2. Freely branching habit.
3. Dark green-colored leaves.
4. Large inflorescences with showy red purple-colored flowers.

5. Resistance to Powdery Mildew.
6. Good garden performance.

Plants of the new Crepe Myrtle can be compared to plants of the female parent, 'Zuni'. Plants of the new Crepe Myrtle differ primarily from plants of 'Zuni' in the following characteristics:

1. Plants of the new Crepe Myrtle are faster growing than plants of 'Zuni'.
2. Plants of the new Crepe Myrtle have darker green-colored leaves than plants of 'Zuni'.
3. Plants of the new Crepe Myrtle have darker purple-colored flowers than plants of 'Zuni'.

Plants of the new Crepe Myrtle can be compared to plants of the *Lagerstroemia indica* 'Catawba', not patented. In side-by-side comparisons conducted in San Antonio, Tex., plants of the new Crepe Myrtle differed primarily from plants of 'Catawba' in the following characteristics:

1. Plants of the new Crepe Myrtle were faster growing than plants of 'Catawba'.
2. Plants of the new Crepe Myrtle had darker green-colored leaves than plants of 'Catawba'.
3. Plants of the new Crepe Myrtle and 'Catawba' differed in flower color as plants of 'Catawba' had violet purple-colored flowers.

BRIEF DESCRIPTION OF THE PHOTOGRAPHS

The accompanying colored photographs illustrate the overall appearance of the new Crepe Myrtle, showing the colors as true as it is reasonably possible to obtain in colored reproductions of this type. Colors in the photographs may differ slightly from the color values cited in the detailed botanical description which accurately describe the colors of the new Crepe Myrtle plant.

The photograph on the first sheet is a side perspective view of a typical plant of 'Bradberry's Wine' grown in a container in an outdoor nursery.

The photograph on the second sheet is a close-up view of typical inflorescences of 'Bradberry's Wine'.

DETAILED BOTANICAL DESCRIPTION

The aforementioned photographs and following observations, measurements and values describe plants grown in San Antonio, Tex. during the summer in an outdoor nursery and under conditions which closely approximate commercial production. During the production of the plants, day temperatures ranged from 20° C. to 35° C. and night temperatures ranged from 15° C. to 22° C. Plants had been growing for three and two years when the photographs and the description, respectively, were taken. In the following description, color references are made to The Royal Horticultural Society Colour Chart, 2007 Edition, except where general terms of ordinary dictionary significance are used.

Botanical classification: *Lagerstroemia indica* 'Bradberry's Wine'.

Parentage:

*Female, or seed, parent.*—*Lagerstroemia indica* 'Zuni', not patented.

*Male, or pollen, parent.*—Unknown selection of *Lagerstroemia indica*, not patented.

Propagation:

*Type.*—By softwood cuttings.

*Time to initiate roots.*—About 14 to 18 days at 32° C.

*Time to produce a rooted young plant.*—About six weeks at 32° C.

*Root description.*—Medium to thick, fibrous; tan in color.

*Rooting habit.*—Moderate branching; moderately dense to dense.

Plant description:

*Plant form and growth habit.*—Shrub; upright to somewhat outwardly spreading plant habit; moderately vigorous growth habit.

*Branching habit.*—Freely branching habit with lateral branches potentially developing at every node.

*Plant height.*—About 1 m.

*Plant diameter* (*area of spread*).—About 52 cm.

Lateral branch description:

*Length.*—About 51 cm.

*Diameter.*—About 7 mm.

*Internode length.*—About 2 cm.

*Strength.*—Strong.

*Texture.*—Smooth, glabrous.

*Color, immature.*—Close to 187A.

*Color, mature.*—Close to N199B.

Foliage description:

*Arrangement.*—Alternate, simple.

*Length.*—About 5.5 cm.

*Width.*—About 3.9 cm.

*Shape.*—Elliptical.

*Apex.*—Acute.

*Base.*—Obtuse.

*Margin.*—Entire.

*Texture, upper surface.*—Smooth, glabrous.

*Texture, lower surface.*—Mostly smooth and glabrous with pubescence along veins.

*Venation pattern.*—Pinnate, arcuate.

*Color.*—Developing and fully expanded leaves, upper surface: Darker than N137A; venation, close to 146B. Developing and fully expanded leaves, lower surface: Close 137B; venation, close to 146C.

*Petiole.*—Length: About 2.5 mm. Diameter: About 1.5 mm. Texture, upper and lower surfaces: Smooth, glabrous. Color, upper surface: Close to 146B. Color, lower surface: Close to 146C.

Flower description:

*Flower appearance/arrangement.*—Showy ruffled flowers arranged in terminal panicles. Freely flowering habit with usually about 72 flowers per inflorescence. Flowers face mostly upright.

*Flower longevity.*—Flowers last for about three days on the plant; flowers not persistent.

*Natural flowering season.*—Summer and autumn in Texas.

*Fragrance.*—Not detected.

*Inflorescence height.*—About 17.5 cm.

*Inflorescence diameter.*—About 9 cm.

*Flower diameter.*—About 3.2 cm.

*Flower length* (*height*).—About 1.7 cm.

*Flower bud.*—Length: About 6 mm. Diameter: About 5 mm. Shape: Obovate. Texture: Smooth, glabrous. Color: Close to 146A.

*Petals.*—Arrangement/quantity: Single semi-circular whorl of six petals with a long stalk at the base. Lobe length: About 1.1 cm. Lobe width: About 1.2 cm. Stalk length: About 6.5 mm. Stalk diameter: About 1 mm. Shape: Roughly orbicular. Apex: Rounded, crenulate. Margin: Crenulate, ruffled. Texture, upper and lower surfaces: Smooth, glabrous; satiny. Color: When opening and fully opened, upper surface: Close to 70A; color does not fade with development. When opening and fully opened, lower surface: Close to 70A.

*Sepals.*—Arrangement/quantity: Single whorl of six fused sepals. Length: About 9 mm. Width: About 4 mm. Shape: Elliptical. Apex: Acute. Margin: Entire. Texture, upper and lower surfaces: Smooth, glabrous. Color: When opening, upper surface: Close to 157A. When opening, lower surface: Close to 146A. Fully opened, upper surface: Close to 157A. Fully opened, lower surface: Close to 146A slightly tinged with close to 59A.

*Pedicels.*—Length: About 7 mm. Diameter: About 1.5 mm. Strength: Strong, flexible. Texture: Smooth, glabrous. Color: Close to 146A slightly tinged with close to 59A.

*Reproductive organs.*—Androecium: Quantity per flower: About 18. Anther shape: Bi-lobed. Anther length: About 1 mm. Anther color: Close to 12A. Amount of pollen: Moderate. Pollen color: Close to 14A. Gynoecium: Quantity per flower: One. Pistil length: About 1.1 cm. Style length: About 1 cm. Style color: Close to 185B. Stigma appearance: Rounded. Stigma color: Close to 146A.

*Fruits.*—Type: Loculicidal capsule. Quantity: One per flower. Length: About 1.1 cm. Diameter: About 8.5 mm. Texture: Smooth, glabrous. Color: Close to 146A.

*Seeds.*—Length: About 2.5 mm. Diameter: About 2 mm. Color: Close to 154D.

Garden performance: Plants of the new Crepe Myrtle have been observed to have good garden performance and to tolerate rain, wind and temperatures ranging from about −12 C. to about 43° C.

Pathogen/pest resistance: Plants of the new Crepe Myrtle have been observed to be resistant to Powdery Mildew. Plants of the new Crepe Myrtle have not been shown to be resistant to pests and other pathogens common to Crepe Myrtle.

It is claimed:

1. A new and distinct Crepe Myrtle plant named 'Bradberry's Wine' as illustrated and described.

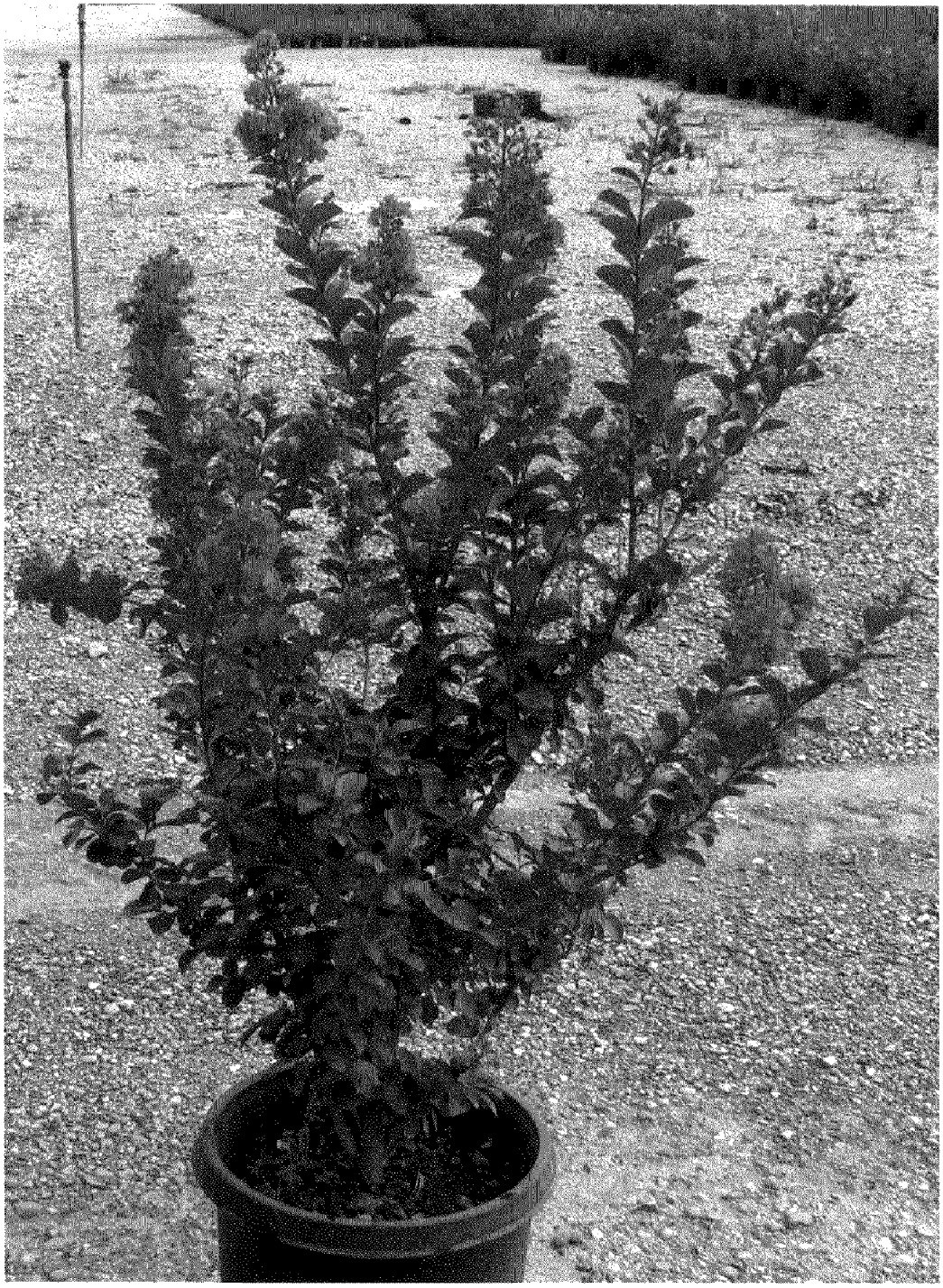

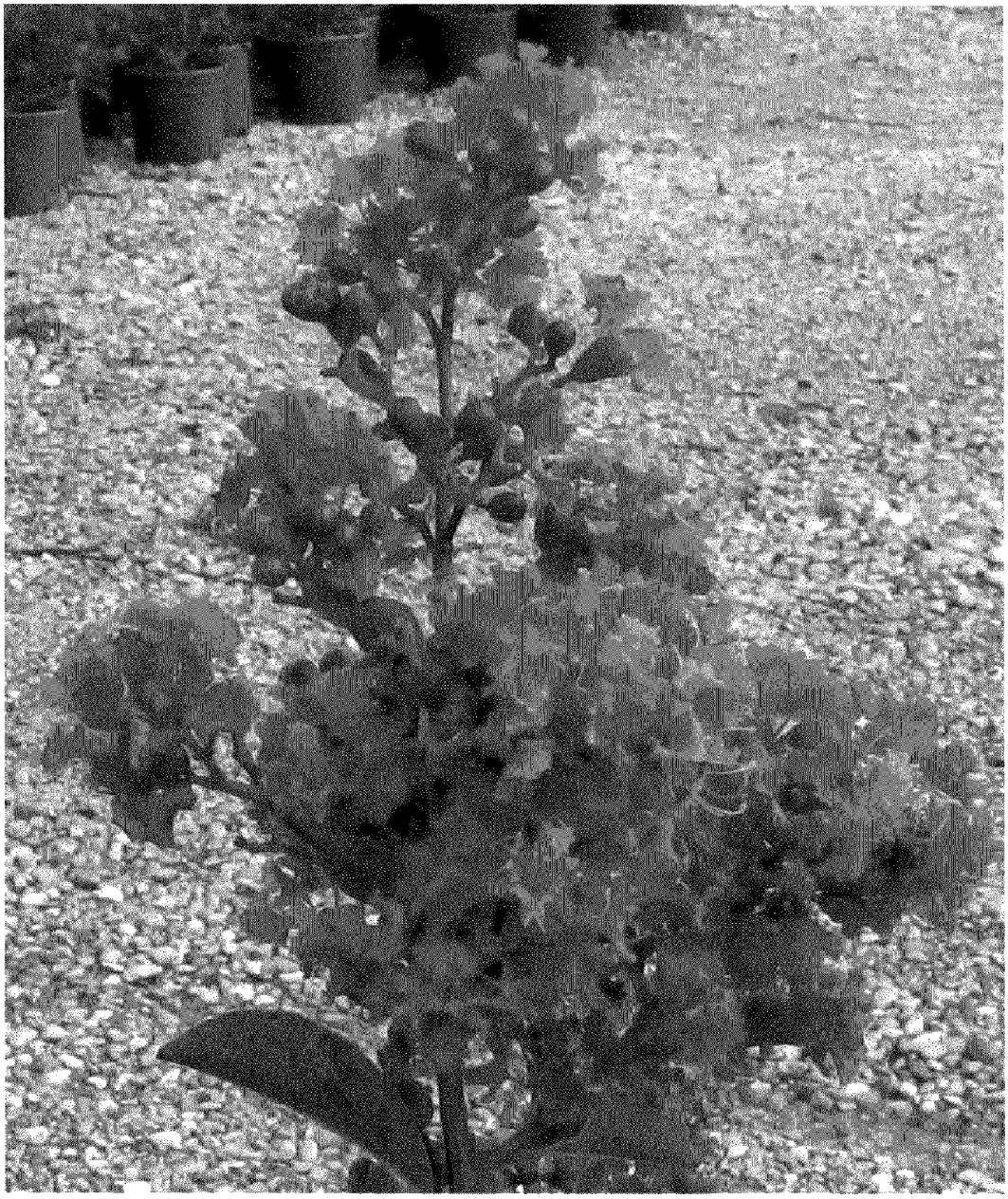

* * * * *